United States Patent [19]

Convert et al.

[11] 4,312,364
[45] Jan. 26, 1982

[54] APPARATUS FOR LOCALIZED HEATING OF A LIVING TISSUE, USING ELECTROMAGNETIC WAVES OF ULTRA HIGH FREQUENCY, FOR MEDICAL APPLICATIONS

[75] Inventors: Guy Convert; Félix Diamand; Jacques Dufour, all of Buc; Jean-Paul Le Bourgeois, Paris, all of France

[73] Assignee: C.G.R. MeV, Buc, France

[21] Appl. No.: 893,814

[22] Filed: Apr. 5, 1978

[30] Foreign Application Priority Data

Apr. 8, 1977 [FR] France ............................... 77 10756

[51] Int. Cl.³ ............................................. A61N 1/40
[52] U.S. Cl. ..................... 128/804; 128/736
[58] Field of Search ........... 128/404, 407, 408, 419 R, 128/421, 422, 2 H, 736, 804, 784–786, 399

[56] References Cited

U.S. PATENT DOCUMENTS

| | | | |
|---|---|---|---|
| 2,407,690 | 9/1946 | Southworth | 128/422 |
| 2,728,337 | 12/1955 | Guillemin, Jr. | 128/2 H |
| 4,016,886 | 4/1977 | Doss et al. | 128/422 |
| 4,108,147 | 8/1978 | Kantor | 128/404 |
| 4,108,163 | 8/1978 | Fleckenstein et al. | 128/2 H |
| 4,138,998 | 2/1979 | Nowogrodzki | 128/736 X |

FOREIGN PATENT DOCUMENTS

| | | | |
|---|---|---|---|
| 1143937 | 7/1960 | Fed. Rep. of Germany | 128/404 |
| 1161362 | 1/1964 | Fed. Rep. of Germany | 128/804 |
| 1648905 | 5/1971 | Fed. Rep. of Germany | 128/804 |
| 2109515 | 9/1972 | Fed. Rep. of Germany | 128/804 |
| 2356183 | 10/1974 | Fed. Rep. of Germany | 128/404 |
| 2407559 | 8/1975 | Fed. Rep. of Germany | 128/404 |
| 1188490 | 4/1970 | United Kingdom | 128/404 |

OTHER PUBLICATIONS

Davis, "Microwaves Score TKO Cancer", Microwaves, vol. 15, No. 10, pp. 14, 16, Oct. 1976.
Larsen et al., "A Microwave . . . Transducer", IEEE Trans. on Microwave Theory & Tech., vol. 22, No. 4, pp. 438–444, Apr. 1974.
Barrett et al., "Subcutaneous Temp. . . . Sensing", Science, vol. 190, pp. 669, 670, 687, Nov. 1975.
Ely et al., "Heating Characteristics . . . Microwaves", IEEE Trans BME, pp. 123–135, Oct. 1964.

*Primary Examiner*—Lee S. Cohen
*Attorney, Agent, or Firm*—Oblon, Fisher, Spivak, McClelland & Maier

[57] ABSTRACT

An apparatus for thermal treatment of the human body, using electromagnetic waves (200 to 2500 Mc/s) and radiometric receivers for monitoring and possibly controlling the temperature reached by the living tissues. A generator at ultra high frequency delivers a power of about one Watt into a coaxial cable terminated by a probe emitting electromagnetic waves in the organ to be heated by dielectric losses in the medium. A multichannel receiver, switched at intervals, analyzes the radiation reemitted by the living tissues through the probe, then utilized as a receiving antenna. The temperature reached in a region surrounding the probe is deduced therefrom and can be utilized for controlling the power emitted through a servocontrol system.

10 Claims, 11 Drawing Figures

APPARATUS FOR LOCALIZED HEATING OF A LIVING TISSUE, USING ELECTROMAGNETIC WAVES OF ULTRA HIGH FREQUENCY, FOR MEDICAL APPLICATIONS

This invention relates to an apparatus for localised heating of a living thing using electromagnetic waves of very high frequency and to the use of this apparatus in medicine.

It is known that the local heating of an organ or of part of an organ, applied either on its own or in conjunction with another medical treatment, such as radiotherapy or chemotherapy, can have significant therapeutic effects.

Various means for locally heating a surface zone of the human body are already known. The process known as diathermy is used for organs situated deep inside the body and consists in connecting a short-wave generator operating for example at a frequency of 13.5 or 27 Mc/s to two electrodes forming capacitors which are applied on either side of the organ to be heated.

Now the difficulties involved in using and the disadvantages attending the known means are various:

The increase in temperature of the various regions of the organ is difficult to determine, complex relations existing between the heating time, the nature of the living tissue and the temperature reached. It is generally accepted that a temperature of 47° C. should not be locally exceeded which, even over a short period, results in necrosis of the living tissues.

In the case of diathermy, it is possible to a certain extent to delimit the region to be heated by varying the shape and size of the electrodes. However, the dimensions of the region subjected to heating are necessarily of the order of magnitude of the distance between the electrodes with the result that, depending upon the region of the body in question, the heated volume may be much greater than is desirable.

In addition, it is not possible to control the distribution of the heating temperature. Thus for example the energy per unit volume which is dissipated into a fatty tissue is much greater than that dissipated into a muscular tissue. An effect such as this can make the apparatus ineffectual in certain cases because a given temperature in a given tissue can only be reached at the expense of necrosis of the adjacent tissues.

The present invention obviates some of the difficulties referred to above whilst at the same time affording the following advantages:

very precise localization of the region subjected to heating;

simultaneous measurement of the maximal temperature of the hottest point.

According to the invention, there is provided an apparatus for localized heating of living tissues, using electromagnetic waves of ultra high frequency, comprising an ultra high frequency generator, a transmission line, a probe capable of emitting said waves and designed for being introduced into the medium to be heated, and radiometric means for monitoring the temperature of said medium and/or living tissues in contact with said probe.

The invention will be better understood and other features thereof will become apparent from the following description in conjunction with the accompanying drawings, wherein:

FIG. 1a diagrammatically illustrates one example of embodiment of an apparatus according to the invention, comprising a radiometry receiver;

FIG. 1b is a block diagram of one embodiment of a radiometric receiver shown in FIG. 1a according to the invention;

FIG. 2 diagrammatically illustrates one example of an arrangement for calibration of the radiometric means;

Figure 1A:
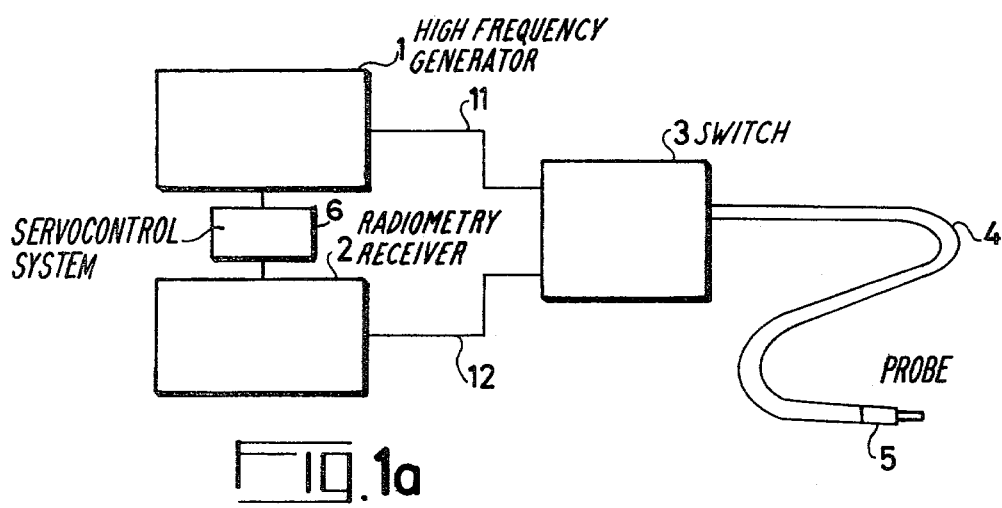
Figure 1B:
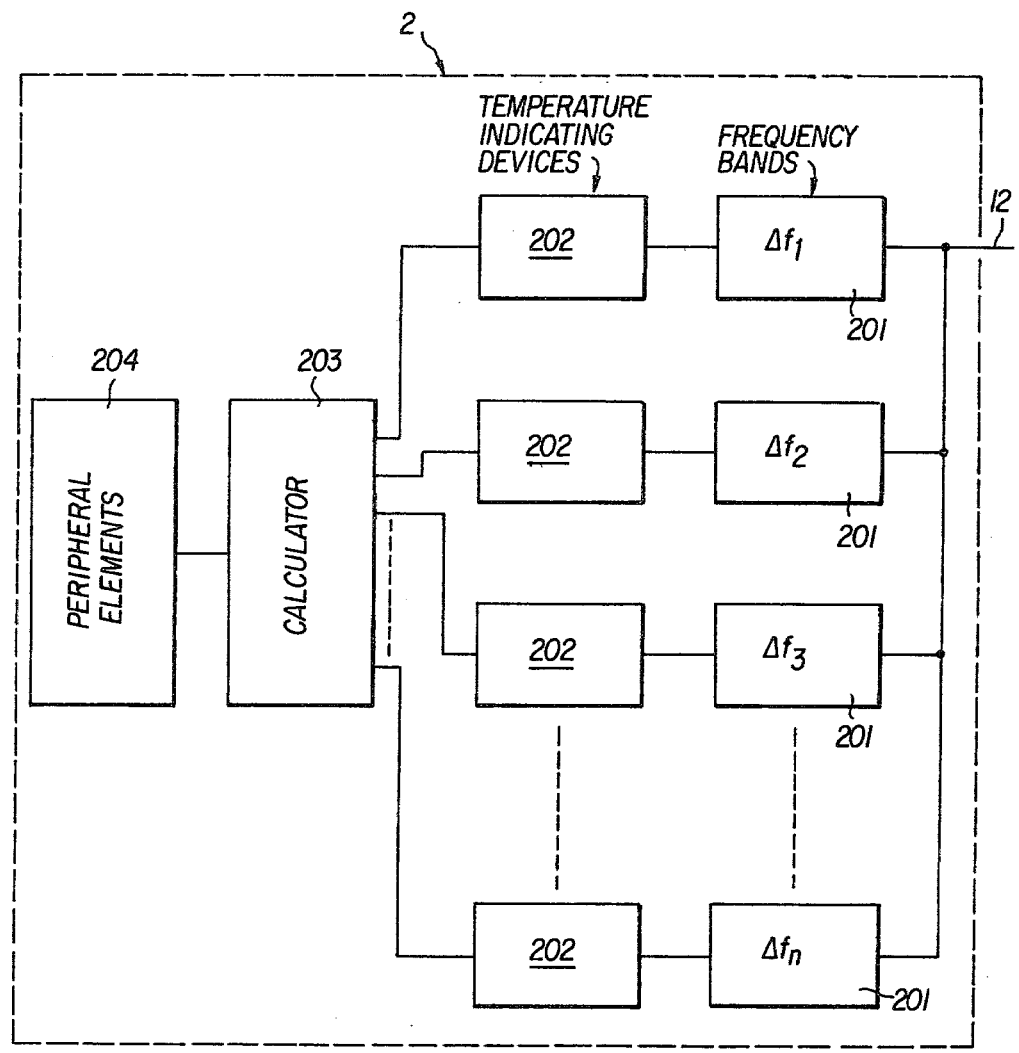

In the embodiment of the apparatus shown in FIG. 1, the means for supplying electrical energy at ultra high frequency to a probe 5 are diagrammatically represented by an ultra high frequency generator 1 connected to the probe by a line 11, for example of the coaxial type, a switch 3 and a coaxial cable 4.

The generator transmits into line 11 a fixed or variable frequency for instance in the range from 200 to 2500 MHz. In cases where a single generator is used, it may be provided with a system for periodically varying the frequency (wobulator) under the control of a program of the data-processing type for effecting a time-sharing of the frequencies generated.

Where several generators are combined in the same apparatus, they may operate either simultaneously or successively under the control of a program of the data-processing type because, as will be explained hereinafter, the penetration of the waves emitted by the probe depends upon the frequency according to a law which depends upon the type of probe. Various probes are described hereinafter.

The switch 3 enables the line 11 to be disconnected from and the cable 4 to be connected to a radiometry receiver 2 via line 12. A receiver such as this, of conventional type, comprises several radiometric devices operating in different frequency bands 201, each band having a corresponding temperature indicator 202. In a receiver of this type, the measuring apparatus giving the noise levels existing in each band are directly graduated in degrees of temperature. In addition, it is possible to provide the receiver with a calculator 203 and with peripheral elements 204 giving the temperature distribution in a region surrounding the probe. By means of a five-band receiver equipped with a calculator, it would be possible to record five temperatures at different distances from the probe. For example, a measuring time of the order of one second should be sufficient for measuring the maximum temperature to a fraction of a degree in a frequency band with limits of 0.2 to 2F, F being the frequency of the heating waves.

Figure 2:
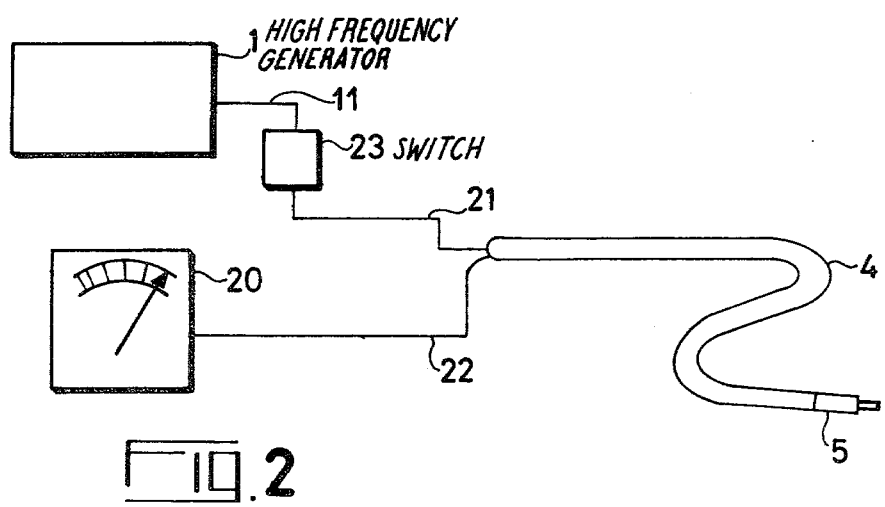

The arrangement shown in FIG. 2 is a calibrating device for radiometry receiver. The same elements as in FIG. 1 have been denoted by the same reference numerals, but the probe 5 contains a system with a thermocouple incorporated therein which will be described hereinafter. This system is connected by a twin-wire line 22 to a thermometric volt meter 20. The coaxial pair of the cable 4 is connected by a coaxial cable 21 to the generator 1 via a switch 23.

It is possible to control the heating in the apparatus of FIG. 1 and the arrangement of FIG. 2 by providing the device with a conventional servocontrol system 6.

Figure 3:
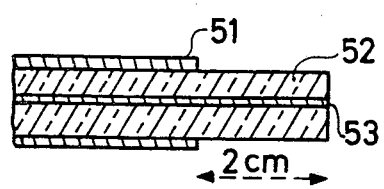
FIGS. 3 to 6 are diagrammatic sections through examples of probes forming part of the apparatus according to the invention.
Figure 4:
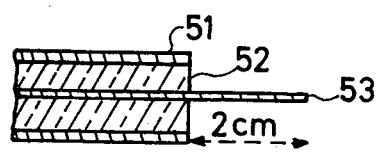
Figure 5:
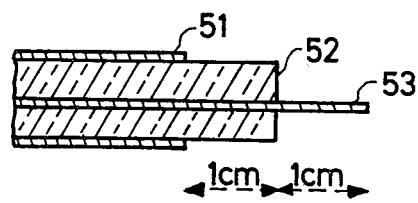
Figure 9:
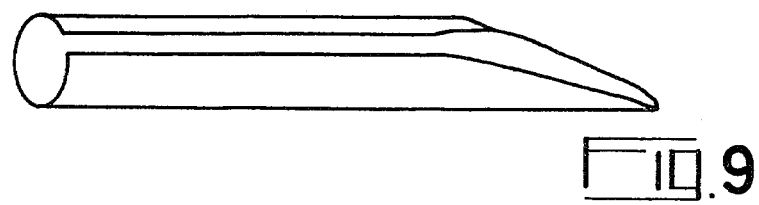
FIG. 9 shows an insertion vehicle for introducing a probe.

The three probes shown in FIGS. 3 to 5 are examples of embodiment designed to pierce the skin and to penetrate the living tissues of the human body. Their introduction may be facilitated by a needle acting as a so-called "insertion vehicle" (FIG. 9) of which the diameter may be very small, i.e. of the order of 1 millimeter. The probe and the coaxial cable which it extends have a diameter of, for example, 0.85 mm and are introduced into the vehicle before insertion into the human body. After penetration and positioning of the assembly as a whole, the insertion vehicle is carefully withdrawn by sliding it along the coaxial cable.

A probe of the type shown in FIG. 3 is obtained simply by cutting a small-diameter coaxial cable from which the outer conductor 51 is removed over a length of, for example, 2 centimeters. The dielectric 52 is an organic compound which is solid at the temperature of the human body, for example polytetrafuloroethylene. The inner conductor 53 acts as an antenna emitting the electromagnetic waves into the living tissue, the bare dielectric acting as an impedance matcher between the antenna and the propagation medium.

The probes shown in FIGS. 4 and 5 are variants in which the central conductor 53 is exposed either over the entire length of the antenna or over half its length, the outer conductor being removed over a length of the same order as in FIG. 3. The choice of the length of the antenna is made in dependence upon the characteristic impedance of the coaxial cable and the frequency of the electromagnetic radiation (for example 2 cm for a cable having a characteristic impedance of 50 ohms in a range from 300 to 2500 Mc/s).

Figure 7:
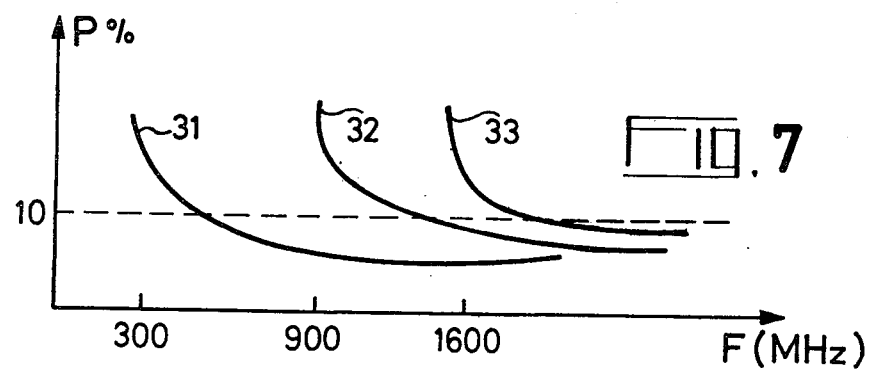
FIG. 7 is an explanatory diagram.

FIG. 7 is a graph showing the fraction of the reflected power (in %) for the probes shown in FIGS. 3 to 5 in dependence upon the frequency emitted by the generator. It can be seen that the three corresponding curves each have an exponentially decreasing part which intersects a linear 10% ordinate at a point situated:

between 300 and 400 Mc/s for the curve 31 (probe of FIG. 3);
between 900 and 1500 Mc/s for the curve 32 (probe of FIG. 4);
between 1800 and 2000 Mc/s for the curve 33 (probe of FIG. 5).

From this it follows that the percentage of total energy dissipated into the organ in the form of heat (by dielectric losses) is very high (above 90%) when the frequency exceeds a minimum frequency characteristic of the type of probe used for a cable having a given impedance characteristic and for a given tissue.

By contrast, it is possible with the same probe to obtain different depths of penetration by varying the frequency, whence the advantage of using a generator generating a variable frequency output under the control of a data program.

Figure 6:
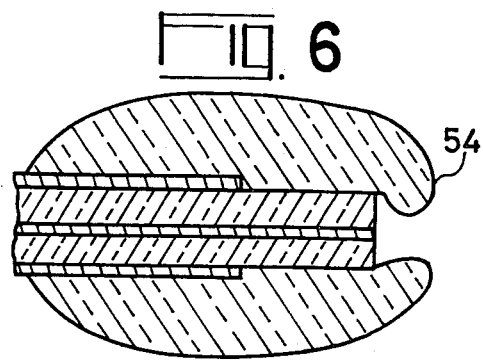

The probe shown in FIG. 6 is of a different type designed for introduction into the human body by a natural route, for example the oesophagus. The only difference between the probe shown in FIG. 6 and the preceding probes lies in the presence of an ovoidal sleeve made of a dielectric material selected for its physical properties (particularly its permittivity which is similar to that of the dielectric 52) and chemical properties (harmlessness to living tissue), for example silicone.

Figure 8:
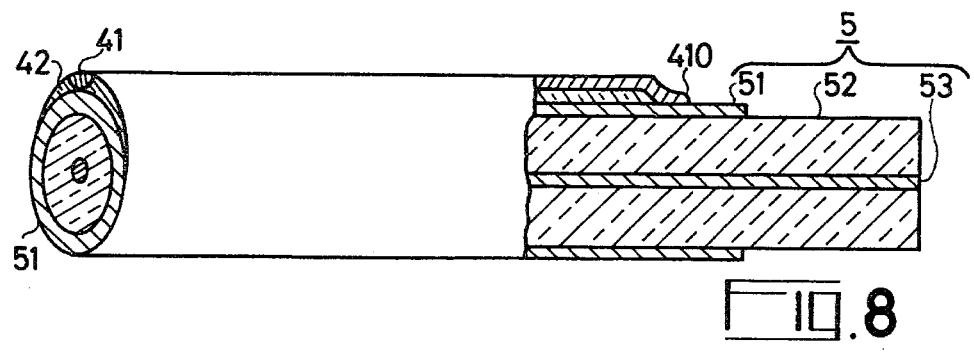
FIG. 8 is a diagrammatic section through one example of a proble with a thermocouple incorporated therein.

FIG. 8 shows a thermocouple system incorporated in the cable 4 feeding a probe 5. A wire 41 made of the copper (60%) nickel (40%) alloy is arranged at the periphery of the cable 4, being isolated by a dielectric 42 from the outer conductor 51 of the coaxial line. In the immediate vicinity of the probe 5, this wire is welded at 410 to the outer conductor 51. The wire 41 emerges at the other end of the cable 42 where it is connected to a first conductor of the two-conductor line 22 symbolised by a single line (FIG. 2), the second conductor of this line being connected to the conductor 51. By virtue of the thermometric voltmeter described above, a system such as this makes it possible to measure the temperature prevailing at the actual location of the probe.

Figure 10:
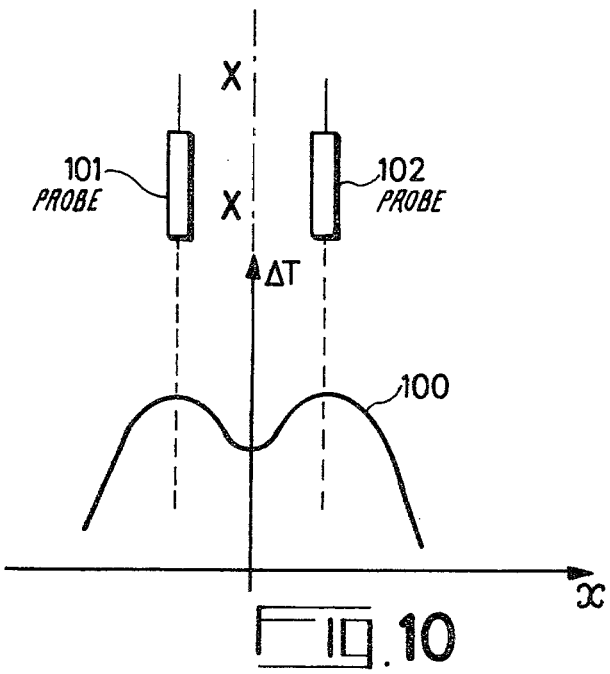
FIG. 10 is an explanatory diagram.

FIG. 10 relates to a system comprising two probes 101 and 102 arranged parallel to one another in an organ to be treated. These two probes may be introduced by using a system comprising two insertion vehicles fixed parallel to one another by a metallic plate to which their bases are welded, leaving the points of the needles free.

XX represents the axis of symmetry of the system of two probes. If the distances from this axis, measured along an axis Ox, of the various points of the organ to be treated are recorded as abscissae and the temperature difference T between the temperature of the various points of the heated region and the normal temperature of the organ to be treated as ordinates along a perpendicular axis, a curve 100 is obtained. A curve such as this has two rounded peaks corresponding to the respective locations of the two probes. It can be seen that the heated region is considerably enlarged and that the temperature is rendered uniform to a certain extent. It is also possible to use systems comprising three or four insertion vehicles fixed parallel to one another in the same way as in the two-vehicle system.

Where several probes are used, they are each connected in parallel by a coaxial cable optionally provided with a thermocouple to the high frequency generator, if necessary with interposition of a switch.

What we claim is:

1. An apparatus for localized heating of living tissues, using electromagnetic waves of ultra-high frequency comprising an ultra-high frequency generator, a transmission line having one end connected to said ultra-high frequency generator, a switch with two inputs and one output, one input being connected to another end of said transmission line, a probe connected to the output of said switch, said probe capable of emitting said ultra-high frequency waves and designed for being introduced into living tissues to be heated, and radiometric means for monitoring the temperature of said living tissues in contact with said probe, said radiometric means comprising a radiometry receiver connected to the other input of said switch, said receiver capable of measuring the electromagnetic radiation re-emitted by said living tissues and picked up by said probe.

2. An apparatus as claimed in claim 1, wherein said transmission line is of the coaxial type and designed to be introduced with the probe into the living tissues to be heated.

3. An apparatus as claimed in claim 2, wherein said probe comprises:
a coaxial cable having an outer conductor and an inner conductor separated by a solid dielectric, the outer conductor of said cable being removed over a length of the order of half the wavelength of the radiation of said generator.

4. An apparatus as claimed in claim 2, wherein said probe comprises:
   a coaxial cable having an outer conductor and an inner conductor separated by a solid dielectric, the outer conductor of said cable being removed over a length of the order of half the wavelength of the radiation of the generator, and at least a part of said dielectric being bare over at least a part of the length of said probe.

5. An apparatus as claimed in claim 2, wherein the probe comprises a coaxial cable including an outer conductor and an inner conductor separated by a dielectric wherein the dielectric of said coaxial cable is polytetrafluorethylene.

6. An apparatus as claimed in claim 1, wherein said probe is surrounded by a sleeve of dielectric material.

7. An apparatus as claimed in claim 6, wherein said sleeve is made of silicone.

8. An apparatus as claimed in claim 1, wherein said radiometry receiver is of the type comprising several frequency bands and comprises a temperature indicator corresponding to each of said frequency bands.

9. An apparatus as claimed in claim 8, wherein said radiometry receiver additionally comprises a calculator and peripheral elements connected thereto giving the distribution of temperatures in a region surrounding said probe.

10. An apparatus as claimed in claim 1, further comprising a servocontrol system for controlling the power delivered by the ultra-high frequency generator to the probe based on the temperature measured by the receiver, said servocontrol system being connected to said radiometry receiver and to said ultra-high frequency generator.

* * * * *